United States Patent [19]

Monaco

[11] 4,256,102

[45] Mar. 17, 1981

[54] SUBCUTANEOUS DIALYSIS SYSTEM

[76] Inventor: Anthony P. Monaco, 73 Brackett Rd., Newton, Mass. 02158

[21] Appl. No.: 38,777

[22] Filed: May 14, 1979

[51] Int. Cl.³ .......................................... A61M 25/00
[52] U.S. Cl. ............................... 128/213 A; 128/348
[58] Field of Search ............ 128/213 A, 214 R, 214.4, 128/215, 348–350

[56] References Cited

U.S. PATENT DOCUMENTS

| 3,520,298 | 7/1970 | Lange | 128/213 A |
| 3,633,585 | 1/1972 | McDonald | 128/348 |
| 3,640,269 | 2/1972 | Delgado | 128/348 X |
| 3,971,376 | 7/1976 | Wichterle | 128/260 |
| 4,160,454 | 7/1979 | Foux | 128/348 |
| 4,184,497 | 1/1980 | Kolff et al. | 128/213 A |

Primary Examiner—Dalton L. Truluck
Attorney, Agent, or Firm—Wolf, Greenfield & Sacks

[57] ABSTRACT

A means and method of peritoneal dialysis in which a dialyzing tube is permanently embedded in a patient's body with a perforated end of the tube located within the peritoneal cavity and the other end secured subcutaneously at the fascia. Dialyzing is achieved by perforating the epidermis with a needle at the time of dialysis and thereafter introducing a dialyzing fluid through the needle, and if desired, through a catheter inserted through a needle into the tube in quantity and for a time period to permit dialyzing. The dialyzing fluid containing contaminants is then removed by siphon and/or gravity action through the needle. The sequence of introducing and removing fluid may be repeated and thereafter the needle withdrawn allowing the epidermis to heal and leaving no visible appearance of the dialyzing tube.

5 Claims, 2 Drawing Figures

SUBCUTANEOUS DIALYSIS SYSTEM

SUBJECT MATTER OF INVENTION

The present invention relates to a means and method for peritoneal dialysis.

BACKGROUND OF INVENTION

The common usage of dialyzing machines is now being partially replaced by a dialysis system which involves introducing dialyzing fluids into the peritoneal cavity of the body. In this system, an elongated tube is secured with a perforated end within the peritoneal cavity and the other end projecting through the epidermis. One or more flanges along the tube between the peritoneum and the epidermis are designed to provide biological barriers. Dialyzing fluid is introduced into the body by opening the external ends of the tube and passing a dialyzing fluid through the tube into the cavity for a time period and in quantities sufficient to permit contaminants from the blood to mix across the peritoneal membrane with the dialyzing fluid. The dialyzing fluid is then removed by siphon or a gravity technique and the procedure is repeated. This system is used for both acute and chronic dialysis problems. While the short term nature of an acute peritoneal dialysis procedure usually minimizes the problems usually inherent in this technique, chronic peritoneal dialysis does pose a number of problems which are not satisfied by the presently available techniques. In this prior art technique the dialyzing tube is normally secured to the fascia and the peritoneum by suturing a porous flange designed to provide a biological seal at the point at which the tube passes through the fascia and peritoneum. This system also provides, in many instances, a second biological seal at a position laterally spaced from the first and under the fat layers. The tube then exists through the epidermis where it is closed until required. This arrangement is frequently uncomfortable to a patient because the tube projects permanently from the patient's body at some point in the abdominal wall. In addition, this system poses a serious infection problem. The open end of the tube provides a permanent entrance site for possible infection. This, in turn, requires a great deal of care by the patient in making sure the tube is closed at all times when not in use. But even if the patient is careful, bacteria may enter the tube when hooking up the tube to the dialyzing fluid. The patient, moreover, must be especially careful when taking showers or swimming and, in many instances, will refrain from both of these activities in fear of introducing infection through the tube. There is also some basis for believing that bacteria pass down the outer wall of the tube and through the biological barriers before these biological barriers have been fully integrated with the surrounding tissue.

Since the portion of the tube projecting from the patient's body is normally held against the body with a bandage over a long period of time, there is always a potential source of localized skin problems caused by the adhesive bandage securing the tube end. Furthermore, this projecting tube also creates cosmetic and psychological problems for the patient. These psychological problems are particularly acute in patients with kidney problems that require many hours of dialysis every week for indefinite periods of time.

A further common complication in peritoneal dialysis using systems of this type is bleeding primarily from the abdominal wall. At times this requires additional suturing or transfusions. When bleeding is substantial, the catheter frequently becomes plugged. Peritonitis is also a common result of contamination of the tubing or from poor placement of the catheter. Consequent infection rates are occasionally as high as ten percent.

There is also some evidence of experimental efforts to provide subcutaneous peritoneal dialysis by embedding a tube and chamber under the skin. This arrangement involves the use of a tube extending into the peritoneal cavity with an elongated bulky rigid tube member secured subcutaoneously. This system appears to have been experimental and, if implanted, was proved unacceptable for a variety of reasons. The bulk and rigidity of the tube makes it difficult to implant and secure. It would also be very uncomfortable and likely to cause serious trauma to the patent because of its size, shape and rigidity.

SUMMARY OF THE INVENTION

The limitations of the prior art, as described above, are in large measure overcome by the present invention. It is an object of the present invention to provide peritoneal dialysis for chronic dialyzing in which the likelihood of biological infection is signifcantly reduced. A further object of the present invention is to provide a peritoneal dialyzing method and means in which the patient is not subject to physical limitations which, for example, would prevent or limit his ability to take showers or to swim. A further object of the present invention is to provide an improved peritoneal dialysis means and method in which the cosmetic limitations of past systems are elinated and psychological problems minimized.

A still further object of this invention is to provide an improved peritoneal dialysis system which is comfortable for the patent and which is not likely to cause trauma. It is also easy to use and, with the tube, easy to locate for dialyzing.

In the present invention there is provided an elongated peritoneal tube having one end perforated and secured within the peritoneal cavity. The other end of this tube is open and preferably flared. This open end is secured subcutaneously just outside the fascia and peritoneum. Dialyzing is effected by introducing dialyzing fluid into the tube by puncturing the epidermis with a tubular needle and positioning the end of the needle within the open end of the tube. A dialyzing fluid is passed through the needle directly or, if desired by a catheter, into the peritoneal tube in a quantity and over a time period sufficient to permit dialysis. After an appropriate time period, the dialyzing fluid is removed by siphon and gravity action and the process is repeated a desired number of times before the needle is withdrawn. When the needle is withdrawn, the puncture is antiseptically cleaned and covered with a bandage. Under normal conditions this puncture will heal promptly.

BRIEF DESCRIPTION OF DRAWINGS

The foregoing objects and advantages of the present invention will be more clearly understood when considered in conjunction with the accompanying drawings in which.

DETAILED DESCRIPTION OF PRESENT INVENTION

Figure 1:
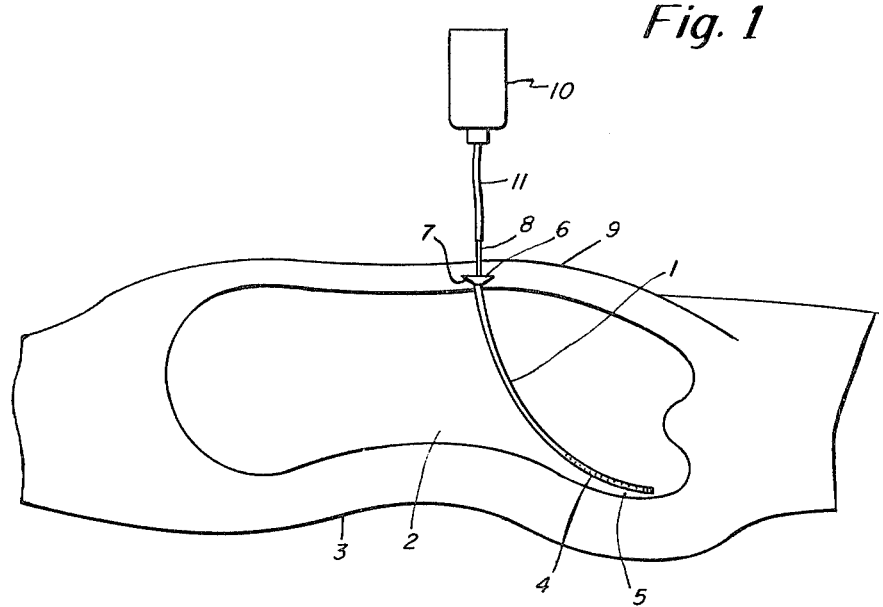
FIG. 1 is a schematic illustration of a human body showing the location of the peritoneal tube embodying and used in connection with the present invention.

The present invention is designed primarily for chronic peritoneal dialysis. In this system, the peritoneal tube 1 is permanently surgically inserted in the peritoneal cavity of a patient 3. Preferably, the tube 1 has a perforated section 4 extending into the cul-de-sac portion 5 of the peritoneal cavity. The other end of the tube 1 is formed with an opening 6 preferably at the end of the funnel section 7, as more fully described hereafter, to receive a needle 8 which is inserted through the epidermis 9 at the time of dialyzing. A suitable quantity of dialyzing fluid 10 is introduced into the peritoneal cavity through a tube 11 which connects to the needle 8. The fluid 10 passes through the tube 11, needle 8 and into the peritoneal tube 1 where it is dispersed through the perforations in section 4. If desired, a catheter may be used. This catheter with an outer diameter sufficiently small to pass through the needle 8 is threaded through the needle and into the peritoneal tube 1 down at least a portion of the tube 1 to the perforated sections. The other end of the catheter may be connected to the fluid container or to any other suitable fluid supply.

Figure 2:
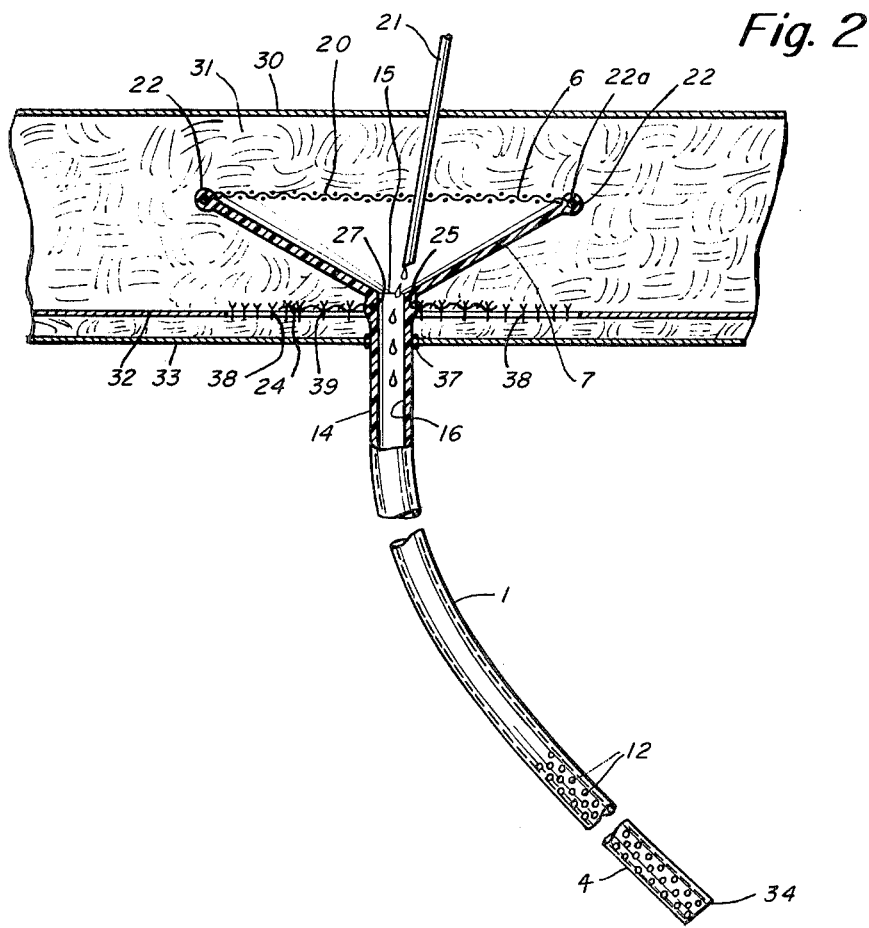
FIG. 2 is a fragmentary cross-sectional view of a peritoneal tube embodying and used in connection with the present invention.

Referring to FIG. 2, there is shown a more detailed drawing of the peritoneal tube. The tube may vary in length, depending upon the particular size of the patient in which it is to be secured. It may, for example, come in a selection of lengths, such as, for example, lengths of 15, 18 and 20 centimeters. The diameter of these tubes may also vary depending upon the particular application for which it is intended. A typical tube may have an outer diameter of 5 millimeters with a wall thickness of 1 millimeter and, consequently, an inner diameter of 3 millimeters. This diameter, however, may be increased as required to a convenient maximum, as for example, in the range of 10 millimeters as an outer diameter with an inner diameter of 8 millimeters. The outer diameter may typically be much larger than the peritoneal tubes heretofore in use because peritoneal tubes of the type heretofore in use were normally inserted with the use of a trocar. Since those tubes must be inserted through the trocar, the inner diameter of the trocar was the limiting factor to the maximum size of the peritoneal tube. In the present invention, the insertion of the peritoneal tube does not contemplate the use of a trocar and therefore, the outer diameter of the tube can be substantially greater than the diameter of the peritoneal tubes heretofore in use. This in turn means that there is less likelihood of tubes clogging after prolonged use, as is the case with the type of tube heretofore in use.

The lower end of the tube 1 is provided with a plurality of perforations 12. These perforations may vary in diameter, but preferably are in the order of 1 millimeter and are designed to permit the easy flow of fluid between the interior of tube 1 and the peritoneal cavity. The number of perforations may vary but typically will cover the lower half of the tube 1 and will be suitably arranged radially about it at a distance apart of 3 or 4 millimeters.

The lower portion 4 of the tube 1 is integrally formed with an upper portion 14 formed with an opening 16. Preferably the opening 15 is formed as a funnel 7 by a frustoconic section. The lower portion of the funnel is integrally formed with the upper portion of the upper section 15 of a tube 1. The tube 1 and funnel section 7 are preferably molded of a suitable inert, flexible, durable, resilient and soft surgical grade plastic such as silicon. This integrally molded tube and funnel is formed with a continuous smooth inner surface 16 having, as noted above, an inner diameter in the order of 3 to 6 millimeters in the tubular section and flared uniformly to an outer diameter in the order of 40 to 70 millimeters at the wide end of the funnel section 7. The height of the frusto-conic or funnel section 7 is preferably in the order of from 10 to 20 millimeters.

The open end of the funnel section 7 is covered with a needle perforable nylon mesh 20 that is designed to allow the tip 21 of needle 8 to be forced between the interstices of the mesh without damaging it, but at the same time provide a means for preventing fat or other tissue from moving into the interior of the funnel section 7. This nylon mesh may be woven with a range of mesh openings, but mesh openings in the order of a fraction of a millimeter are preferable. The mesh should be tight enough to hold the dialyzing fluid in the tube after fibrous ingrowth has sealed the mesh but sufficiently open to permit a needle to be forced through the interstices without damaging the mesh. The periphery of the mesh 20 is suitably anchored at the periphery of the funnel section 7 by suitable means. This may include, for example, molding the funnel section 7 with its periphery integral with the periphery of the mesh 20 so that the periphery 22 of the mesh is bonded to the periphery of the funnel section. Other suitable plastic mesh material may also be used.

An anchoring cuff 24 preferably formed of Dacron is also integrally formed with the unit. In this arrangement, the cuff 24, preferably in the shape of an annular collar, is formed preferably of Dacron fabric molded with its inner annular edge 25 bonded within the wall of the unit at the junction of the funnel section 7 and tube 14. Preferably, the wall may be slightly thickened at this junction as illustrated at 27.

This peritoneal tube is surgically emplanted within the peritoneal cavity by conventional surgical techniques in which an incision is made through the epidermis 30, fat layer 31, fascia 32 and peritoneum 33. This incision is made conventionally below the navel and at the midline of the fascia so as to avoid cutting the rectus muscle. The lower end 4 of the tube 1 is inserted into the peritoneal cavity with the extreme end 34 positioned, if possible, within the cul-de-sac 5 of the peritoneal cavity. The funnel section 7 is subcutaneously positioned preferably at the level of the fascia. The peritoneal layer 33 is suitably sutured with a purse string suture 37 to secure the peritoneum about the upper end 14 of the tube 1. The fascia 32 is then suitably sutured along the incision at 38. The cuff 24 is also sutured at 30 to the fascia 32. Thereafter the subcutaneous fat layer is sutured over the funnel and then the epidermis is also sutured and the incision allowed to heal.

After the surgical incision has healed, the patient, when not being dialyzed, has no outward signal of the peritoneal tube. When it is necessary to dialyze the patient, the wide end of the funnel section is manually located, the area over it antiseptically prepared and a needle is then pushed through the epidermis until its pointed end enters the funnel section 7. With the patient in a prone position, dialyzing fluid is then introduced through the needle 21 into the funnel 7 and is allowed to flow downwardly through the tube 1 and out through the openings 12 into the peritoneal cavity. After an appropriate quantity of fluid is introduced, as for example two liters, and an appropriate time period for dialyzing has passed, as for example twenty minutes, the container 10 from which the dialyzing fluid was introduced through the needle is lowered below the level of the body and the fluid within the peritoneal cavity is then forced by siphoning and gravitational action, as well as body movement from the peritoneal cavity outwardly through the tube 1, needle 21 and back into the fluid container 10. The now contaminated dialyzing fluid is removed and a fresh supply introduced into the body. This process is repeated a prescribed number of times until the dialyzing cycle is completed. At that time, the needle is withdrawn, the wound cleaned and a small bandage placed over it. Since these wounds are limited to the diameter of the hypodermic needle 21, they heal quickly, thus permitting repeated dialysis in the same general area without ill effect. Further, the prompt healing of this wound prevents bacteria from entering tube 1. If desired, a catheter having an outer diameter smaller than the inner diameter of the needle 21 may be threaded through the needle 21 after it has been inserted in the body. The catheter may then be snaked down through the needle and into the tube 1, thus permitting introduction of dialyzing fluid through the catheter into the tube 1.

Having now described my invention, I claim:

1. A means for peritoneal dialysis comprising an elongated tube having an opening at one end and perforations formed along a section thereof, means for securing said tube with said perforations within the peritoneal cavity and with said one end subcutaneous but external of said peritoneal cavity, and means forming a perforable diaphragm over said open end, comprising a solid wall member having a frustoconic shape with the smaller diameter end of said frustoconic shape connected to said one end and the larger diameter end of said frustoconic shape supporting a needle perforable diaphragm.

2. A means as set forth in claim 1 wherein said perforable diaphram is formed of a mesh.

3. A means as set forth in claim 2 wherein said means for securing comprises a cuff extending radially from said tube and adapted to be sutured to the peritoneum.

4. A means as set forth in claim 3 wherein said perforations are formed radially about the tube.

5. A means as set forth in claim 4 wherein the height of said frustoconic shape is between 10 and 20 millimeters.

* * * * *